(12) United States Patent
Kannengiesser et al.

(10) Patent No.: US 11,861,827 B2
(45) Date of Patent: Jan. 2, 2024

(54) TECHNIQUES FOR AUTOMATICALLY CHARACTERIZING LIVER TISSUE OF A PATIENT

(71) Applicant: Siemens Healthcare GmbH, Erlangen (DE)

(72) Inventors: Stephan Kannengiesser, Wuppertal (DE); Berthold Kiefer, Erlangen (DE); Tommaso Mansi, Plainsboro, NJ (US); Marcel Dominik Nickel, Herzogenaurach (DE); Thomas Pheiffer, Philadelphia, PA (US)

(73) Assignee: Siemens Healthcare GmbH, Erlangen (DE)

( * ) Notice: Subject to any disclaimer, the term of this patent is extended or adjusted under 35 U.S.C. 154(b) by 325 days.

(21) Appl. No.: 17/168,545

(22) Filed: Feb. 5, 2021

(65) Prior Publication Data

US 2021/0248741 A1    Aug. 12, 2021

(30) Foreign Application Priority Data

Feb. 6, 2020    (EP) .................................... 20155782

(51) Int. Cl.
*G06K 9/00*    (2022.01)
*G06T 7/00*    (2017.01)
(Continued)

(52) U.S. Cl.
CPC ............ *G06T 7/0012* (2013.01); *A61B 5/055* (2013.01); *A61B 5/4244* (2013.01);
(Continued)

(58) Field of Classification Search
None
See application file for complete search history.

(56) References Cited

U.S. PATENT DOCUMENTS

2011/0257505 A1    10/2011    Suri
2013/0144160 A1    6/2013    Sakuragi
(Continued)

FOREIGN PATENT DOCUMENTS

CN    106204587 A    12/2016
CN    108806793 A    11/2018
(Continued)

OTHER PUBLICATIONS

Pan Ki Kim et al.: "Myocardial T1 and T2 Mapping: Techniques and Clinical Applications", Korean Journal of Radiology: Official Journal of the Korean Radiological Society, vol. 18, No. 1, Jan. 1, 2017 (Jan. 1, 2017), p. 113, XP055714688, ISSN: 1229-6929, DOI: 10.3348/kjr.2017.18.1.113.
(Continued)

*Primary Examiner* — Wei Wen Yang
(74) *Attorney, Agent, or Firm* — Banner & Witcoff Ltd.

(57) ABSTRACT

The disclosure relates to techniques for automatically characterizing liver tissue of a patient, comprising receiving morphological magnetic resonance image data set and at least one magnetic resonance parameter map of an imaging region comprising at least partially the liver of the patient, each acquired by a magnetic resonance imaging device, via a first interface. The techniques further include applying a trained function comprising a neural network to input data comprising at least the image data set and the parameter map. At least one tissue score describing the liver tissue is generated as output data, which is provided using a second interface.

20 Claims, 5 Drawing Sheets

(51) Int. Cl.

| | | |
|---|---|---|
| *G16H 10/60* | (2018.01) | |
| *G16H 30/20* | (2018.01) | |
| *G16H 50/20* | (2018.01) | |
| *A61B 5/055* | (2006.01) | |
| *A61B 5/00* | (2006.01) | |
| *G01R 33/48* | (2006.01) | |
| *G01R 33/56* | (2006.01) | |
| *G06N 3/08* | (2023.01) | |
| *G06N 3/045* | (2023.01) | |

(52) U.S. Cl.
CPC ........ *A61B 5/7267* (2013.01); *G01R 33/4828* (2013.01); *G01R 33/5608* (2013.01); *G06N 3/045* (2023.01); *G06N 3/08* (2013.01); *G16H 10/60* (2018.01); *G16H 30/20* (2018.01); *G16H 50/20* (2018.01); *A61B 2576/02* (2013.01); *G06T 2207/10088* (2013.01); *G06T 2207/20081* (2013.01); *G06T 2207/20084* (2013.01); *G06T 2207/30056* (2013.01)

(56) References Cited

U.S. PATENT DOCUMENTS

| 2014/0330106 | A1 | 11/2014 | Banerjee et al. |
|---|---|---|---|
| 2017/0032090 | A1 | 2/2017 | Kamen et al. |
| 2017/0061620 | A1 | 3/2017 | Park et al. |
| 2017/0350952 | A1 | 12/2017 | Kiefer et al. |
| 2018/0182101 | A1* | 6/2018 | Petersen .................. G06T 7/11 |
| 2018/0204045 | A1* | 7/2018 | Feiweier ............ G06V 40/1365 |
| 2018/0260957 | A1 | 9/2018 | Yang et al. |
| 2019/0183429 | A1 | 6/2019 | Sung et al. |
| 2020/0000362 | A1 | 1/2020 | Wallace et al. |
| 2020/0335214 | A1* | 10/2020 | Garteiser ........... G01R 33/4828 |
| 2021/0233645 | A1* | 7/2021 | Morard ................. G06T 7/0014 |

FOREIGN PATENT DOCUMENTS

| CN | 109859841 A | 6/2019 | |
|---|---|---|---|
| CN | 109934832 A | 6/2019 | |
| WO | WO-2013082677 A1 * | 6/2013 | ............ A61B 5/055 |
| WO | 2015144916 A1 | 10/2015 | |
| WO | 2019191059 A1 | 10/2019 | |
| WO | 2019200753 A1 | 10/2019 | |
| WO | 2019241266 A1 | 12/2019 | |

OTHER PUBLICATIONS

Kleiner, David E. et al.: "Design and Validation of a Histological Scoring System for Nonalcoholic Fatty Liver Disease" in Hepatology, vol. 41, No. 6, 2005, pp. 1313-1321.

A. Kendall and Y. Gal; "What uncertainties do we need in bayesian deep learning for computer vision?"; Advances in neural information processing systems; pp. 5574-5584; 2017; and.

European Search Report dated Jul. 24, 2020, Application No. 20155782.4.

He Lan et al; "Automatic Liver Segmentation Based on Three-Dimensional Convolutional Neural Network"; Chinese Journal of Medical Physics; No. 06; published Jun. 25, 2018.

Wang, Yan et al; "Application of Convolution Neural Network In Image Classification of Liver Puncture"; Computer Knowledge and Technology; No. 25; published Sep. 5, 2018; ISSN 1009-3044.

* cited by examiner

TECHNIQUES FOR AUTOMATICALLY CHARACTERIZING LIVER TISSUE OF A PATIENT

CROSS-REFERENCE TO RELATED APPLICATIONS

The present application claims the benefit of the filing date of European patent application no. EP20155782.4, filed on Feb. 6, 2020, the contents of which are incorporated herein by reference in their entirety.

TECHNICAL FIELD

The present disclosure relates to a computer-implemented method and characterization system for automatically characterizing liver tissue of a patient, a computer program and an electronically readable storage medium.

BACKGROUND

Magnetic resonance imaging (MRI) allows for different imaging techniques to gather different morphological, structural, functional, and parameter-related information about an imaged object. With the establishment of quantitative MRI, even quantitative parameter maps of a region of interest of an object can be determined. This makes MRI an important tool in medical diagnostics.

However, to cope with the large quantity of information yielded from magnetic resonance examinations, computer-implemented analysis tools are often employed by medical staff. Such computer programs automatically evaluate magnetic resonance data and provide evaluation results, which may be used to improve diagnostics by a physician. Such practice is referred to as computer-aided or computer-assisted diagnostics (CAD). Often, the characterization of certain tissue types in patients is of interest, for example regarding inflammation processes, lesions, and the like. A computer-aided analysis tool may, for example, estimate tissue characterization scores, which can then be used by clinicians for diagnosis and to guide treatment.

For example, in patients with nonalcoholic fatty liver disease (NAFLD), fat accumulates in the liver. This can lead to a more severe form of NAFLD called nonalcoholic steatohepatitis (NASH), in which inflammation and cell damage occur in the liver. Some patient's progress to liver fibrosis, cirrhosis, and cancer, and this process at some point becomes irreversible. Often the only way to definitively diagnose NASH is with a liver biopsy, which is an invasive and often painful procedure. There is thus value in developing non-invasive tests which can accurately characterize and stage NASH, as well as predict progression and guide treatment.

SUMMARY

There are a variety of MR imaging techniques which can detect biomarkers associated with NASH and liver disease. These include magnetic resonance sequences to determine fat fraction, iron accumulation associated with liver disease, relaxation times, and magnetic resonance elastography (MRE), which can detect the stiffening of the liver associated with liver damage (e.g. fibrosis).

Conventionally, some approaches regarding the liver tissue and in particular NASH have been proposed, wherein multi-parametric quantitative magnetic resonance data are evaluated. In US 2014/0330106 A1 and WO 2015/144916 A1, methods and systems for multi-parametric magnetic resonance diagnosis and staging of liver disease, and non-invasive detection of inflammation of a visceral organ, respectively, are disclosed. Quantitative parameters like extracellular fluid, iron content, lipid content, and relaxometry data are acquired and evaluated by thresholding. US 2017/0350952 A1 discloses a method and an apparatus for automatic characterization (classification) of liver tissue in a region of interest of a liver of a patient, wherein at least one value tuple of the region of interest of the liver is acquired, the value tuple including at least one T1 value determined from magnetic resonance images of the region of interest, or a reciprocal value thereof, and a T2 or T2* value or a reciprocal value thereof. The value tuple is transferred into a multidimensional parameter space and the characterization of the liver tissue is then performed on the basis of the position of the value tuple in the parameter space, such that certain areas in a corresponding multi-parametric space are associated with certain evaluation results.

These approaches use a small number of quantitative values that are measured using a magnetic resonance device or derived from magnetic resonance images. It is, however, difficult to raise the number of parameters in these methods, in particular since the correlation and mutual interplay of these parameters are not always apparent and clear. Additionally, the larger fraction of the magnetic resonance data and its information are discarded and not used in the evaluation.

It is an object of the embodiments of the current disclosure to provide a more robust and accurate way of determining liver tissue characteristics, e.g. at least one score, in a non-interventional approach, regarding the assessment of NASH for instance.

This object is achieved by providing embodiments as discussed herein that include a method, a characterization system, a computer program, and an electronically readable storage medium as discussed herein and further in the claims.

In the following the solution according to the embodiments of the disclosure is described with respect to the described characterization systems as well as with respect to the methods, computer programs, and electronically readable storage mediums. Features, advantages, or alternative embodiments herein can be assigned to the other objects and vice versa. In other words, embodiments for the providing systems, computer programs, and electronically readable storage mediums can be improved with features described or claimed in the context of the methods. In the case of the system, the functional features of the method are embodied by objective units of the characterization system.

A method for automatically characterizing liver tissue of a patient according to the disclosure comprises:
  receiving at least one morphological magnetic resonance image data set and at least one magnetic resonance parameter map of an imaging region comprising at least partially the liver of the patient, each acquired by a magnetic resonance imaging device, via a first interface,
  in a computation unit, applying a trained function comprising a neural network to input data, the input data comprising at least the image data set and the parameter map, wherein at least one tissue score describing the liver tissue, e.g. regarding inflammation and/or fibrosis and/or the presence of NASH, is generated as output data,
  providing the output data using a second interface.

A characterization system for automatically characterizing liver tissue of a patient according to the disclosure analogously comprises:
- a first interface for receiving at least one morphological magnetic resonance image data set and at least one magnetic resonance parameter map of an imaging region comprising at least partially the liver of the patient, each acquired by a magnetic resonance imaging device,
- a computation unit for applying a trained function comprising a neural network to input data, the input data comprising at least the image data set and the parameter map, wherein at least one tissue score describing the liver tissue is generated as output data,
- a second interface for providing the output data.

It is recognized that not only quantitative parameters describing the relevant tissue of the liver, that is, the parenchymal tissue, are relevant to its characterization, e.g. regarding NASH, but also the morphology, e.g. of the anatomy, which is described by magnetic resonance image data sets. The morphological image data set thus is an anatomical magnetic resonance image data set showing the form and/or structure of the anatomy, such as patterns and/or textures for instance. Artificial intelligence has been found to be the ideal tool to not only extract relevant features from the image data set and the parameter maps as a whole, but preferably also describe the correlation and/or interplay of these features, e.g. regarding quantitative parameter features and structural anatomical features. As will be described in detail below, the neural network employed hence may include at least one convolutional layer (for feature extraction) and at least one dense (e.g. fully connected) layer, to derive the at least one tissue score from these features, e.g. an already known, well defined score from the literature.

In general, a trained function, which can also be termed a function trained by a machine learning algorithm or a trained agent, mimics cognitive functions that humans associate with other human minds. In particular, by training based on training data, the trained function is able to adapt to new circumstances and to detect and extrapolate patterns.

In general, parameters of a trained function can be adapted by means of training. For instance, supervised training, semi-supervised training, unsupervised training, reinforcement learning, and/or active learning can be used. Furthermore, representation learning (an alternative term is "feature learning") can be used. For example, the parameters of the trained functions can be adapted iteratively by several steps of training.

The trained function according to the embodiments of the disclosure comprises a neural network, but may additionally or alternatively comprise other suitable machine learning techniques such as a support vector machine, a decision tree, and/or a Bayesian network, for instance. The trained function may be based on k-means clustering, Q-learning, genetic algorithms, and/or association rules. In an embodiment, the neural network may be a deep neural network trained by deep learning approaches. Furthermore, embodiments include the neural network being implemented as or comprise a convolutional neural network or a convolutional deep neural network. Furthermore, other examples include the neural network being or comprising an adversarial network, a deep adversarial network, and/or a generative adversarial network.

The image data set and the parameter map may be acquired using the same or different magnetic resonance imaging devices. The imaging regions of the at least one image data set and the at least one parameter map may be the same or different. For instance, the at least one first imaging region of the image data set may be different from the at least one second imaging region of the parameter map, while multiple first and second imaging regions may also differ. However, all imaging regions contain at least partly the liver tissue to be characterized, e.g. the parenchymal tissue. In some embodiments, a region of interest (ROI) to be analyzed by the trained function is segmented in all image data sets and all parameter maps (e.g. automatically), as known in the state of the art. The region of interest may be determined by segmenting the tissue to be characterized. The trained function then evaluates the input data only inside the region of interest. The region of interest may be determined in a preprocessing step.

In summary, the embodiments of the present disclosure allow for more accurate analysis of magnetic resonance data of liver tissue, forming an improved basis for a diagnosis performed by medical staff, in particular a physician, using the output data of the trained function at a later time. The method is generalizable to a wider population of patients. Liver biopsies or other interventions can be advantageously omitted or at least reduced in number.

In the literature, several well-defined tissue scores, e.g. regarding biopsies, are available, which can be used as output data regarding the current disclosure. For example, in an article named "Design and Validation of a Histological Scoring System for Nonalcoholic Fatty Liver Disease" by David E. Kleiner et al., in Hepatology 1 (2005), pp. 1313-1321, several scores are defined, including the well-known NAS (NAFLD Activity Score). Preferably, the at least one tissue score of the output data is chosen from the group of NAFLD activity score, a steatosis score, a lobular inflammation score, a hepatocyte ballooning score and a fibrosis score, in particular a fibrosis stage. In particular, at least an inflammation score, preferably the NAS, and a fibrosis score, in particular the fibrosis stage, are determined, as the fibrosis stage adds the most information to the NAS. These types of information can also be considered orthogonal.

It is noted at this point that many observations from manual, in this case visual, analysis of morphological, anatomical magnetic resonance image data sets indicates that fibrosis information can be derived from very fine structures/textures, which a clinician may only be able to reliably detect with a lot of experience. However, those features may be robustly detected by artificial intelligence, in this case the trained function. This is also true for other morphological features in connection with fibrosis or the NAS.

The intended magnetic resonance techniques may comprise those that are primarily designed to evaluate liver disease, although the embodiments of the disclosure are extendable to others not described herein. The at least one image data set may have been acquired using a T1-weighted acquisition, for instance, potentially with fat suppression or separation, or another weighted acquisition. The at least one image data set may comprise at least one image data set obtained by using a fat-water separation technique, e.g. a Dixon technique. Furthermore, the at least one parameter of the at least one parameter map may chosen from the group of a relaxation times, the reciprocal thereof, in particular $R2^*$, an extracellular fluid measure, and a fat fraction.

Magnetic resonance techniques may hence include anatomical scans, T1 and T2 map acquisition, $R2^*$ (or other reciprocal relaxations times) relaxometry-based measurements of iron overload, and proton density fat fraction imaging. However, functional imaging may also be employed and the results evaluated by the trained function.

For example, the input data may additionally comprise a magnetic resonance diffusion-weighted data set and/or a magnetic resonance elastography data set of an imaging region comprising at least partially the liver of the patient. The diffusion-weighted dataset may, for example, be an apparent diffusion coefficient (ADC) map. To take liver stiffness into account, which may, for example, be affected by fibrosis, elastography maps of liver stiffness may also be acquired and used as input data. Such elastography maps are acquired using magnetic resonance elastography (MRE) and sometimes less preferred, since additional measuring equipment is required.

In some embodiments, the input data further comprises at least one additional scalar and/or vector information related to the patient and/or the liver of the patient. Such additional information may, for example, be chosen from the group comprising demographic information, medical history information, and laboratory results. Moreover, the additional scalar and/or vectoral information may be received from an electronic health record of the patient. In this manner, demographic information, medical history, lab values, and similar variables which may be relevant to liver disease may also be taken into account by the trained function.

In an embodiment, the neural network comprises at least one convolutional layer in at least one convolutional partial neural network, e.g. for feature extraction from the image data set and/or the parameter map, and/or at least one fully connected layer in a dense partial neural network, to derive the output data from at least the extracted features. This structure of the neural network allows handling of the multi-dimensional image data sets and parameter maps in the input data and takes into account the mutual correlations of the extracted features in the dense partial neural network. It also allows the convenient use of additional scalar and/or vector information as described above. In an embodiment, if the input data comprises additional scalar and/or vector information, the additional scalar and/or vector information or intermediate data derived therefrom is added to a feature vector generated by the at least one convolutional partial neural network. In other words, the results of the at least one convolutional layer are usually flattened to form a feature vector, which can be further evaluated by the at least one fully connected layer. Additional data can be conveniently added to the end of such a feature vector such that a longer input vector for the dense partial neural network results.

In embodiments, the intermediate data is generated by an additional dense partial neural network having at least one fully connected layer. In a variant in which additional information, e.g. clinical data, is available as input, the model defined by the neural network may be modified by adding an additional series of fully connected layers parallel to the at least one convolution layers. The resulting intermediate data, containing relevant extracted features, is then additionally added to the feature vector in a concatenation step. This allows the trained function to first model correlations which only relate to the additional scalar and/or vector information and extract corresponding relevant features, e.g. by condensing the additional scalar and/or vector information to fewer, relevant intermediate data.

Some variants of the embodiments of the disclosure are conceivable when extracting features from the at least one image data set and the at least one parameter map (termed input data sets in the following) using at least one convolutional partial neural network. In one variant, the various magnetic resonance input data sets may each be subjected to independent single convolutional partial networks. That is, they form multiple inputs to the neural network, each going through a series of convolutional layers to extract abstract features from the appearance of the liver in each magnetic resonance technique. These abstract features are then concatenated together to form the feature vector and (optionally after the addition of the additional information/intermediate data) fed forward into the dense partial neural network, going through a series of fully connected layers and reaching an output layer, which then gives the at least one tissue score. In another variant, the input data sets may also, at least partially, be stacked, wherein each stack is input into a common convolutional partial neural network.

It is generally noted that, in view of the high dimensionality of the input data, the convolutional partial network as well as, if used, the additional dense partial neural network, can be understood as a feature extractor, reducing the dimensionality of the data to be analyzed to focus on features relevant to the characterization of liver tissue. In embodiments, autoencoders or autoencoder concepts may be implemented. This is also true for the optional additional dense partial neural network. In other words, in the first variant as explained above, the convolution partial neural networks and, optionally, the additional dense partial neural network extract expressive features from high-dimensional data. These expressive features, as the feature vector, form the input to the dense partial network yielding the output data.

In an advantageous extension of the embodiments of the current disclosure, the output data may be determined to additionally comprise at least one predictive outcome information, e.g. risk scores for events related to liver tissue. In such embodiments, the trained function, e.g. its artificial neural network, is trained on censored (anonymized) outcomes data to provide a risk assessment for disease progression and response to treatment. In this case, the input data, e.g. a combination of magnetic resonance parenchymal morphological and quantitative features and optionally additional scalar and/or vector information such as clinical data, are recognized to contain underlying information, which may be predictive of the treatment efficacy and overall status of the patient. The outcomes data may be used or used to derive output training data to train the neural network to predict a non-linear risk function for assigning probabilities of the patient experiencing various future events (e.g. development of cirrhosis, liver failure, etc.). For instance, when also determining predictive outcome information, for example risk scores, the feature extraction by the convolutional partial neural networks and, optionally, the additional dense partial neural network becomes important to reduce the dimensionality of the problem to be solved by the at least one dense partial neural network. It is noted that, regarding the risk scores, a second dense partial neural network (in addition to a first dense partial neural network giving the at least one tissue score) may be implemented, which may use a modified feature vector and/or a feature vector, for example, additionally containing the tissue scores.

In an embodiment, the trained function additionally comprises an uncertainty estimation subfunction, which determines at least one uncertainty information regarding the output data, which is provided associated with the output data using the second interface. Such an uncertainty information is useful for a clinician or medical staff in general when interpreting the output data, e.g. regarding a diagnosis. Thus, the trained function may include a module, namely the uncertainty estimation subfunction, which estimates the uncertainty in its determinations. Since the current disclosure is intended to reduce the need for biopsies required for staging diffuse liver disease, it is also important for the user to know in how far the trained function is uncertain in its prediction. If, for example, a certain threshold for an uncertainty value of the uncertainty information is exceeded or if a person studying the output data decides so, a traditional histopathological staging biopsy may be triggered.

In embodiments, the uncertainty estimation subfunction may comprise a Bayesian deep learning model. Such an approach was, for example, proposed in an article by Alex Kendall and Yarin Gal, "What Uncertainties Do We Need in Bayesian Deep Learning for Computer Vision?", 31st Conference on Neural Information Systems (NIPS 2017), pp. 5574-5584. Of course, also other standard methods for estimating neural network prediction uncertainty may be used.

The embodiments according to the disclosure may also include at least one preprocessing step. Preprocessing may comprise standard image processing measures regarding the input data sets, for example intensity normalization, smoothing, noise reduction, and the like. As already explained above, the region of interest to be analyzed by the trained function may be determined as a preprocessing step, e.g. through segmentation and/or detection.

In an embodiment, in a preprocessing step on the computation unit, all image data sets and all parameter maps are registered to each other. This accounts for the fact that the magnetic resonance imaging required for the current disclosure is often performed with some amount of time in between the acquisition of the different image contrasts and parameter maps. Additionally, there is often also patient motion, which may lead to spatial misalignment between pairs of image data sets/parameter maps. On the other hand, the spatial correlation of features in the different input data sets, that is, magnetic resonance techniques, may be relevant for the characterization of the liver tissue, e.g. for the NASH status. The embodiments according to the disclosure may thus comprise a preprocessing step of registering each input data set to the other. This preprocessing step may employ any number of well-known image registration algorithms, such as landmark-based affine registration, or intensity-based deformable registration.

According to the embodiments of the current disclosure, for training the function, known approaches may be used. For instance, an embodiment according to the disclosure or a training method may comprise, to provide the trained function:
    receiving training data comprising training data sets for each training patient of a training patient cohort using a first training interface, each training data set comprising input training data with at least one morphological magnetic resonance image data set and at least one magnetic resonance parameter map of an imaging region comprising at least partially the liver of the respective training patient, each acquired by a magnetic resonance imaging device, and output training data, the output training data comprising the at least one tissue score for the respective training patient,
    training a function based on the input training data and the output training data with a training computation unit,
    providing the trained function using a second training interface.

In embodiments, the output training data is determined using results of a histopathological biopsy of the liver tissue of the respective patient. Furthermore, the training data may be provided anonymized. In the case that also a predictive outcome information, e.g. a risk score, is to be determined as output data, the predictive outcome information of the training output data may be determined using outcomes data, e.g. censored, that is anonymized, outcomes data.

The training method may be performed by a corresponding training system, having the first and second training interfaces and the training computation unit, and be implemented as a training computer program, which may be stored on an electronically readable training storage medium.

A computer program according to the disclosure can, for example, be directly loaded into a storage means of a characterization system and comprises program means to carry out the steps of a characterization method according to the disclosure if the computer program is executed on the characterization system. It is noted that the characterization system may also be included as a part of a control device of a magnetic resonance imaging device, such that image data sets and parameter maps of a patient acquired using the magnetic resonance imaging device can be evaluated regarding the liver tissue, e.g. NASH, on-site.

The computer program according to the embodiments of the present disclosure may be stored on an electronically readable storage medium according to the disclosure, which thus comprises electronically readable control information stored thereon, the control information at least comprising a computer program according to the disclosure and being configured such that, when the electronically readable storage medium is used in an characterization system (e.g. executed by one or more processors, controller, processing circuitry, etc. of the characterization system), result in the characterization system performing a characterization technique (e.g. method) according to the disclosure. The storage medium may be a non-transitional storage medium, for example, a CD-ROM.

It is noted that it is, in principle, also conceivable to use data sets from other imaging modalities, for example CT or ultrasound, as additional input data, although this is less preferred. The embodiments of the current disclosure aim to provide reliable results regarding the liver tissue from a magnetic resonance examination using multiple magnetic resonance techniques alone, such that one non-interventional examination procedure, optionally with additional information from an electronic health record, suffices to characterize the liver tissue with respect to NASH.

BRIEF DESCRIPTION OF THE DRAWINGS/FIGURES

Other objects and features of the present disclosure will become apparent from the following detailed description considered in conjunction with the accompanying drawings. The drawings, however, are only principle sketches designed solely for the purpose of illustration and do not limit the disclosure. The drawings show:

DETAILED DESCRIPTION

Figure 1:
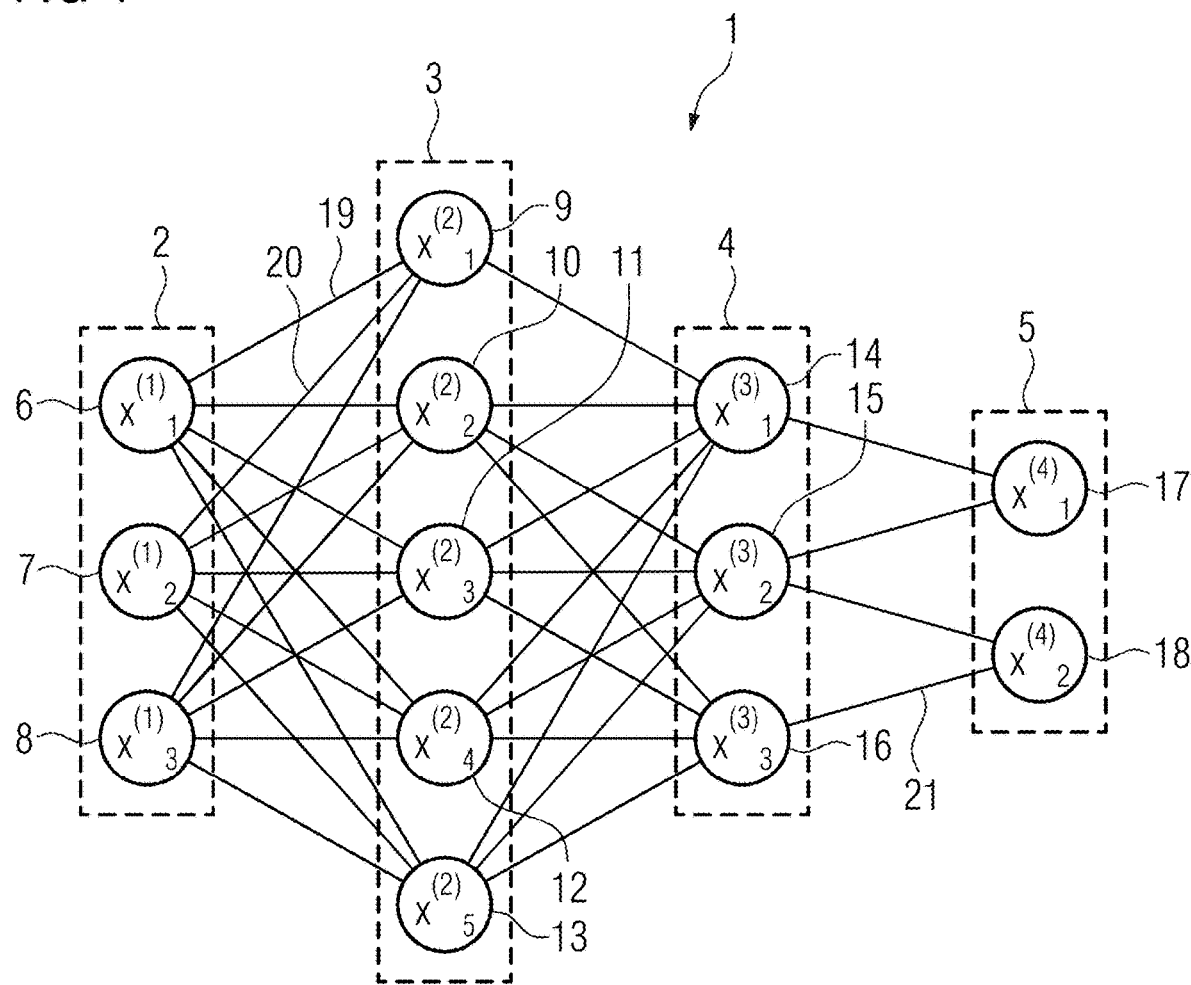
FIG. 1 illustrates an example neural network, in accordance with one or more embodiments of the present disclosure.

FIG. 1 illustrates an example neural network 1, in accordance with one or more embodiments of the present disclosure. Alternative terms for "artificial neural network" include "neural network", "artificial neural net" or "neural net".

The artificial neural network 1 comprises nodes 6-18 and edges 19-21, wherein each edge 19-21 is a directed connection from a first node 6-18 to a second node 6-18. In general, the first node 6-18 and the second node 6-18 are different nodes 6-18, it is also possible that the first node 6-18 and the second node 6-18 are identical. For example, in FIG. 1 the edge 19 is a directed connection from the node 6 to the node 9, and the edge 20 is a directed connection from the node 7 to the node 9. An edge 19-21 from a first node 6-18 to a second node 6-18 is also denoted as "ingoing edge" for the second node 6-18 and as "outgoing edge" for the first node 6-18.

In this embodiment, the nodes 6-18 of the artificial neural network 1 can be arranged in layers 2-5, wherein the layers 2-5 can comprise an intrinsic order introduced by the edges 19-21 between the nodes 6-18. For instance, edges 19-21 may exist only between neighboring layers of nodes 6-18. In the displayed embodiment, there is an input layer 2 comprising only nodes 6-8 without an incoming edge, an output layer 5 comprising only nodes 17, 18 without outgoing edges, and hidden layers 3, 4 in-between the input layer 2 and the output layer 5. In general, the number of hidden layers 3, 4 can be chosen arbitrarily. The number of nodes 6-8 within the input layer 2 usually relates to the number of input values of the neural network, and the number of nodes 17, 18 within the output layer 5 usually relates to the number of output values of the neural network.

For example, a (real) number can be assigned as a value to every node 6-18 of the neural network 1. Here, $x^{(n)}_i$ denotes the value of the i-th node 6-18 of the n-th layer 2-5. The values of the nodes 6-8 of the input layer 2 are equivalent to the input values of the neural network 1, the values of the nodes 17, 18 of the output layer 5 are equivalent to the output value of the neural network 1. Furthermore, each edge 19-21 can comprise a weight being a real number, e.g. the weight is a real number within the interval [−1, 1] or within the interval [0, 1]. Here, $w^{(m,n)}_{i,j}$ denotes the weight of the edge between the i-th node 6-18 of the m-th layer 2-5 and the j-th node 6-18 of the n-th layer 2-5. Furthermore, the abbreviation $w^{(n)}_{i,j}$ is defined for the weight $w^{(n,n+1)}_{i,j}$.

In an embodiment, to calculate the output values of the neural network 1, the input values are propagated through the neural network 1. As an example, the values of the nodes 6-18 of the (n+1)-th layer 2-5 can be calculated based on the values of the nodes 6-18 of the n-th layer 2-5 by Equation 1 below as follows:

$$x_j^{(n+1)}=f(\Sigma_i x_i^{(n)} \cdot w_{i,j}^{(n)}). \qquad \text{Eqn. 1:}$$

Herein, the function f is a transfer function (another term is "activation function"). Known transfer functions are step functions, sigmoid functions (e.g. the logistic function, the generalized logistic function, the hyperbolic tangent, the arctangent function, the error function, the smoothstep function) or rectifier functions. The transfer function is mainly used for normalization purposes.

For example, the values are propagated layer-wise through the neural network 1, wherein values of the input layer 2 are given by the input of the neural network 1, wherein values of the first hidden layer 3 can be calculated based on the values of the input layer 2 of the neural network 1, wherein values of the second hidden layer 4 can be calculated based in the values of the first hidden layer 3, etc.

In order to set the values $w^{(m,n)}_{i,j}$ for the edges 19-21, the neural network 1 has to be trained using training data. For instance, training data may comprise training input data and training output data (denoted as $t_i$). For a training step, the neural network 1 is applied to the training input data to generate calculated output data. As an example, the training data and the calculated output data comprise a number of values, said number being equal to the number of nodes 17, 18 of the output layer 5.

In an embodiment, a comparison between the calculated output data and the training data is used to recursively adapt the weights within the neural network 1 (backpropagation algorithm). For instance, the weights are changed according to Equation 2 below as follows:

$$w_{i,j}^{\prime(n)} = w_{i,j}^{(n)} - \gamma \cdot \delta_j^{(n)} \cdot x_i^{(n)} \qquad \text{Eqn. 2:}$$

wherein γ is a learning rate, and the numbers $\delta^{(n)}_j$ can be recursively calculated using Equation 3 and 4 below as follows:

$$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)}) \qquad \text{Eqn. 3:}$$

based on $\delta^{(n+1)}_j$, if the (n+1)-th layer is not the output layer 5, and $$\delta_j^{(n)} = (x_k^{(n+1)} - t_j^{(n+1)}) \cdot f'(\Sigma_i x_i^{(n)} \cdot w_{i,j}^{(n)}) \qquad \text{Eqn. 4:}$$

if the (n+1)-th layer is the output layer 5, wherein f' is the first derivative of the activation function, and $y^{(n+1)}_j$ is the comparison training value for the j-th node of the output layer 5.

In the following, with respect to FIG. 2, an example of a convolutional neural network (CNN) 22 will be described. Attention is drawn to the fact that the term "layer" that the term "layer" is used in a slightly different way for classical neural networks and convolutional neural networks in the literature. For a classical neural network, the term "layer" refers only to the set of nodes forming a layer (a certain "generation" of nodes). For a convolutional neural network, the term "layer" is often (and in this description) used as an object that actively transforms data, in other words as a set of nodes of the same "generation" and either the set of incoming or the set of outgoing nodes.

Figure 2:
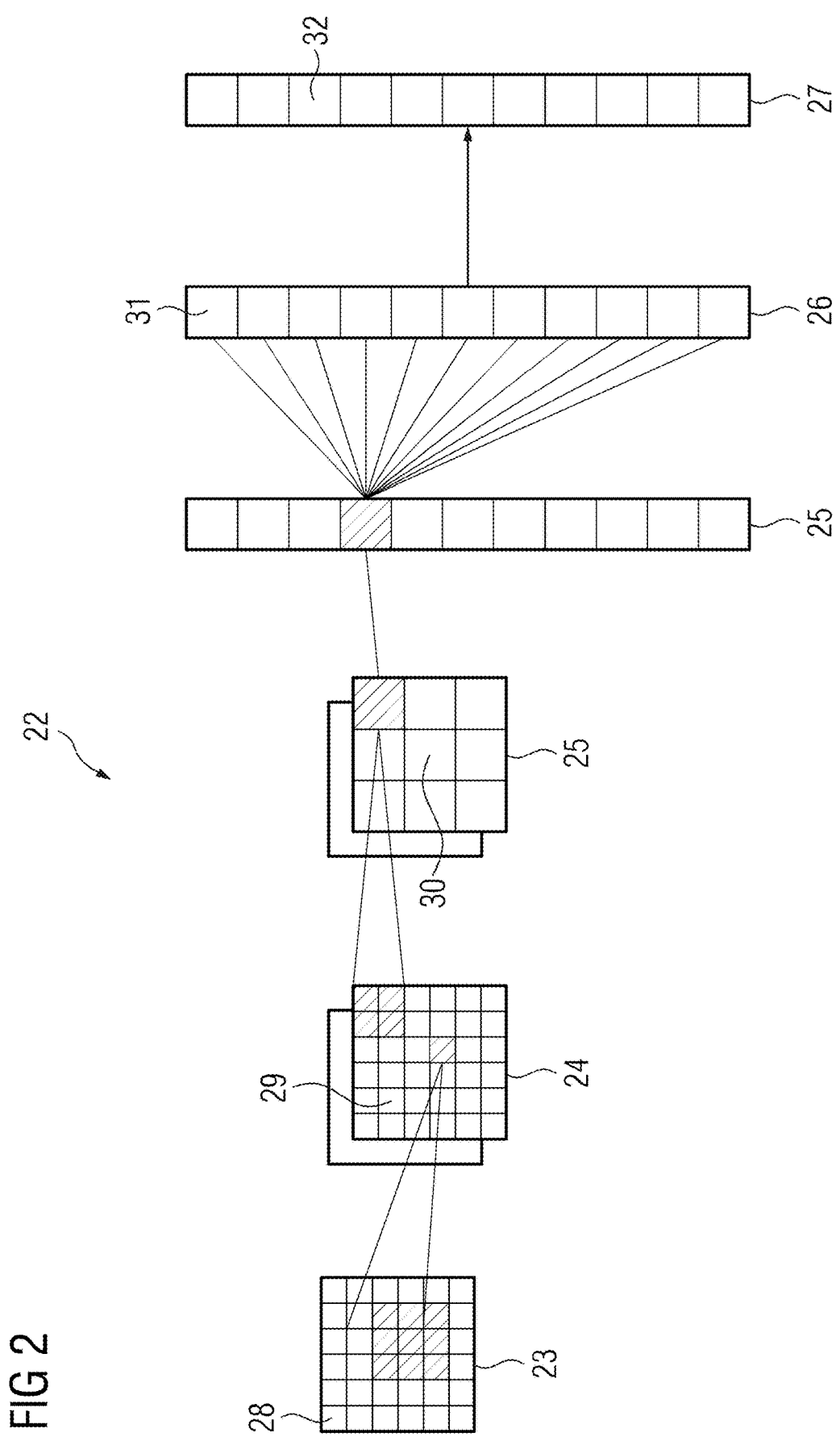
FIG. 2 illustrates an example convolutional neural network, in accordance with one or more embodiments of the present disclosure.

FIG. 2 illustrates an example convolutional neural network 22, in accordance with one or more embodiments of the present disclosure. In this embodiment, the convolutional neural network 22 comprises an input layer 23, a convolutional layer 24, a pooling layer 25, a fully connected layer 26 (also termed dense layer), and an output layer 27. Alternatively, the convolutional neural network 22 can comprise several convolutional layers 24, several pooling layers 25, and several fully connected layers 26 as well as other types of layers. The order of the layers can be chosen arbitrarily. Usually, fully connected layers 26 are used as the last layers before the output layer 27.

As an example, within a convolutional neural network 22 the nodes 28-32 of one layer 23-27 can be considered to be arranged as a d-dimensional matrix or as a d-dimensional image. For instance, in the two-dimensional case the value of the node 28-32 indexed with i and j in the n-th layer 23-27 can be denoted as $x^{(n)}[i,j]$. However, the arrangement of the nodes 28-32 of one layer 23-27 does not have an effect on the calculations executed within the convolutional neural network 22 as such, since these are given solely by the structure and the weights of the edges.

As an example, a convolutional layer 24 is characterized by the structure and the weights of the incoming edges forming a convolution operation based on a certain number of kernels. For instance, the structure and the weights of the incoming edges are chosen such that the values $x^{(n)}{}_k$ of the nodes 29 of the convolutional layer 24 are calculated as a convolution $x^{(n)}{}_k = K_k * x^{(n-1)}$ based on the values $x^{(n-1)}$ of the nodes 28 of the preceding layer 23, where the convolution * is defined in the two-dimensional case as given in Equation 5 below as:

$$x_k^{(n)}[i,j] = (K_k * x^{(n-1)})[i,j] = \Sigma_i \Sigma_j K_k[i',j'] \cdot x^{(n-1)}[i-i', j-j'].\qquad\text{Eqn. 5:}$$

Here, the k-th kernel $K_k$ is a d-dimensional matrix (in this embodiment a two-dimensional matrix), which is usually small compared to the number of nodes 28-32 (e.g. a 3×3 matrix, or a 5×5 matrix). As an example, this implies that the weights of the incoming edges are not independent, but chosen such that they produce said convolution equation. For instance, for a kernel being a 3×3 matrix, there are only 9 independent weights (each entry of the kernel matrix corresponding to one independent weight), irrespectively of the number of nodes 28-32 in the respective layer 23-27. For example, for a convolutional layer 24, the number of nodes 29 in the convolutional layer 24 is equivalent to the number of nodes 28 in the preceding layer 23 multiplied with the number of kernels.

If the nodes 28 of the preceding layer 23 are arranged as a d-dimensional matrix, using a plurality of kernels can be interpreted as adding a further dimension (denoted as "depth" dimension), so that the nodes 29 of the convolutional layer 24 are arranged as a (d+1)-dimensional matrix. If the nodes 28 of the preceding layer 23 are already arranged as a (d+1)-dimensional matrix comprising a depth dimension, using a plurality of kernels can be interpreted as expanding along the depth dimension, so that the nodes 29 of the convolutional layer 24 are arranged also as a (d+1)-dimensional matrix, wherein the size of the (d+1)-dimensional matrix with respect to the depth dimension is by a factor of the number of kernels larger than in the preceding layer 23.

The advantage of using convolutional layers 24 is that spatially local correlation of the input data can exploited by enforcing a local connectivity pattern between nodes of adjacent layers, e.g. by each node being connected to only a small region of the nodes of the preceding layer.

In the present embodiment, the input layer 23 comprises 36 nodes 28, arranged as a two-dimensional 6×6 matrix. The convolutional layer 24 comprises 72 nodes 29, arranged as two two-dimensional 6×6 matrices, each of the two matrices being the result of a convolution of the values of the input layer 23 with a kernel. Equivalently, the nodes 29 of the convolutional layer 24 can be interpreted as arranged in a three-dimensional 6×6×2 matrix, wherein the last dimension is the depth dimension.

A pooling layer 25 can be characterized by the structure and the weights of the incoming edges and the activation function of its nodes 30 forming a pooling operation based on a non-linear pooling function f. For example, in the two-dimensional case the values $x^{(n)}$ of the nodes 30 of the pooling layer 25 can be calculated based on the values $x^{(n-1)}$ of the nodes 29 of the preceding layer 24 in Equation 6 as:

$$x^{(n)}[i,j] = f(x^{(n-1)}[id_1, jd_2], \ldots, x^{(n-1)}[id_1 + d_1 - 1, jd_2 + d_2 - 1])\qquad\text{Eqn. 6:}$$

In other words, by using a pooling layer 25, the number of nodes 29, 30 can be reduced by replacing a number $d_1 \cdot d_2$ of neighboring nodes 29 in the preceding layer 24 with a single node 30 being calculated as a function of the values of said number of neighboring nodes 29 in the preceding layer 24. For instance, the pooling function f can be the max-function, the average or the L2-Norm. For example, for a pooling layer 25 the weights of the incoming edges are fixed and are not modified by training.

The advantage of using a pooling layer 25 is that the number of nodes 29, 30 and the number of parameters is reduced. This leads to the amount of computation in the network 22 being reduced and to a control of overfitting.

In the present embodiment, the pooling layer 25 is a max-pooling layer, replacing four neighboring nodes 29 with only one node 30, the value being the maximum of the values of the four neighboring nodes 29. The max-pooling is applied to each d-dimensional matrix of the previous layer 24; in this embodiment, the max-pooling is applied to each of the two two-dimensional matrices, reducing the number of nodes 29, 30 from 72 to 18.

A fully-connected layer 26 can be characterized by the fact that a majority, e.g. all, edges between nodes 30 of the previous layer 25 and the nodes 31 of the fully-connected layer 36 are present, and wherein the weight of each of the edges can be adjusted individually.

In this embodiment, the nodes 30 of the preceding layer 25 of the fully connected layer 26 are displayed both as two-dimensional matrices, and additionally as non-related nodes 30 (indicated as a line of nodes 30, wherein the number of nodes 30 was reduced for a better presentability). In this embodiment, the number of nodes 31 in the fully connected layer 26 is equal to the number of nodes 30 in the preceding layer 25. Alternatively, the number of nodes 30, 31 can differ.

Furthermore, in this embodiment the values of the nodes 32 of the output layer 27 are determined by applying the Softmax function onto the values of the nodes 31 of the preceding layer 26. By applying the Softmax function, the sum of the values of all nodes 32 of the output layer 27 is 1, and all values of all nodes 32 of the output layer 27 are real numbers between 0 and 1. As an example, if using the convolutional neural network 22 for categorizing input data, the values of the output layer 27 can be interpreted as the probability of the input data falling into one of the different categories.

A convolutional neural network 22 can also comprise a ReLU (acronym for "rectified linear units") layer. For instance, the number of nodes and the structure of the nodes contained in a ReLU layer is equivalent to the number of nodes and the structure of the nodes contained in the preceding layer. As an example, the value of each node in the ReLU layer is calculated by applying a rectifying function to the value of the corresponding node of the preceding layer. Examples for rectifying functions are $f(x) = \max(0, x)$, the tangent hyperbolics function or the sigmoid function.

As an example, convolutional neural networks 22 can be trained based on the backpropagation algorithm. For preventing overfitting, methods of regularization can be used, e.g. dropout of nodes 28-32, stochastic pooling, use of artificial data, weight decay based on the L1 or the L2 norm, or max norm constraints.

Figure 3:
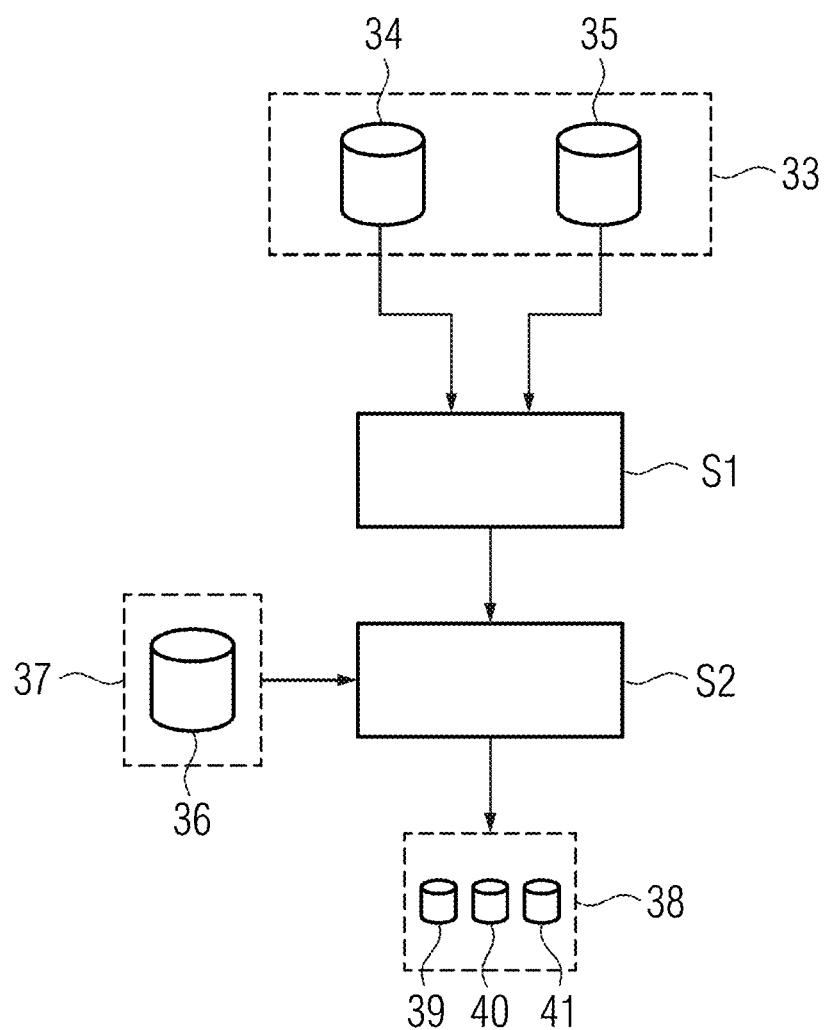
FIG. 3 illustrates an example flowchart of a characterization method, in accordance with one or more embodiments of the present disclosure.

FIG. 3 illustrates an example flowchart of a characterization method, in accordance with one or more embodiments of the present disclosure. The computer-implemented method uses magnetic resonance data of the liver of a patient to determine at least one tissue score characterizing the tissue, which may at a later stage be used for diagnostics and/or therapy by, for example, a physician.

Two sorts of input data sets 33 are used as input data, namely at least one magnetic resonance image data set 34, which is an anatomical image data set 34 showing the morphology of the anatomy, and at least one magnetic resonance parameter map 35, which contains spatially resolved quantitative values of a certain parameter, e.g. from quantitative MRI. The at least one image data set 34 may be acquired using a Dixon technique for fat-water separation and/or may be proton density or relaxation time weighted. It is noted that, in embodiments, at least one of the at least one image data set 34 may be used to determine at least one of the at least one parameter map 35. The at least one parameter map 35 may be or comprise a T1 map, a T2 map, a map of reciprocal values of relaxation times, e.g. R2* as a measure of iron overload, a proton density map describing fat fraction, and the like. Optional further input data sets 33 (not shown in FIG. 3) may comprise functional magnetic resonance data sets, for example an apparent diffusion coefficient map (ADC maps) and/or an elastography map of liver stiffness.

In at least one pre-processing step S1, the input data sets 33 may be registered to each other, to account for movements of the patient and/or different imaging regions and/or pauses in between the application of different magnetic resonance imaging techniques. The registration may be performed landmark-based and/or intensity based and/or affine and/or elastic. In an additional pre-processing step S1, a region of interest, e.g. containing the parenchymal liver tissue of interest, is segmented and/or detected. Known, for instance computer-implemented, segmentation and/or detection algorithms may be implemented.

Pre-processing may further include standard image processing like intensity normalization, noise reduction and/or smoothing.

In a step S2, the input data sets 33 are used as input data for a trained function which comprises a neural network, e.g. a deep convolutional neural network. Further input data may comprise additional scalar and/or vector information 36, in this embodiment provided in an electronic health record 37 of the patient, which is accessible by the computation unit performing the pre-processing and executing the trained function. The additional information 36 may, for example, comprise demographic information, medical history information, and laboratory results.

The trained function uses the input data, regarding the input data sets 33 constrained to the region of interest, to determine output data 38, in this case comprising at least one tissue score 39 and optionally predictive outcome information 40 and uncertainty information 41. The tissue scores 39 in this embodiment at least comprise the NAS and a fibrosis stage, but may also comprise further scores. The predictive outcome information 40 may comprise at least one risk score, for example the probability of a certain event or the success of a certain therapy. The uncertainty information 41 is determined by an uncertainty estimation subfunction using standard methods for uncertainty estimation, for example Bayesian deep learning models.

The neural network of the trained function is trained by using training data sets from a training patient cohort, each training data set comprising input training data, e.g. the input data sets 33 and the additional information 36, as well as output training data for the respective training patient, wherein the tissue scores 39 of the output training data are preferably taken from histopathological liver biopsy results of the respective training patients and the (optional) predictive outcome information 40 is derived from anonymized outcome data.

Figure 4:
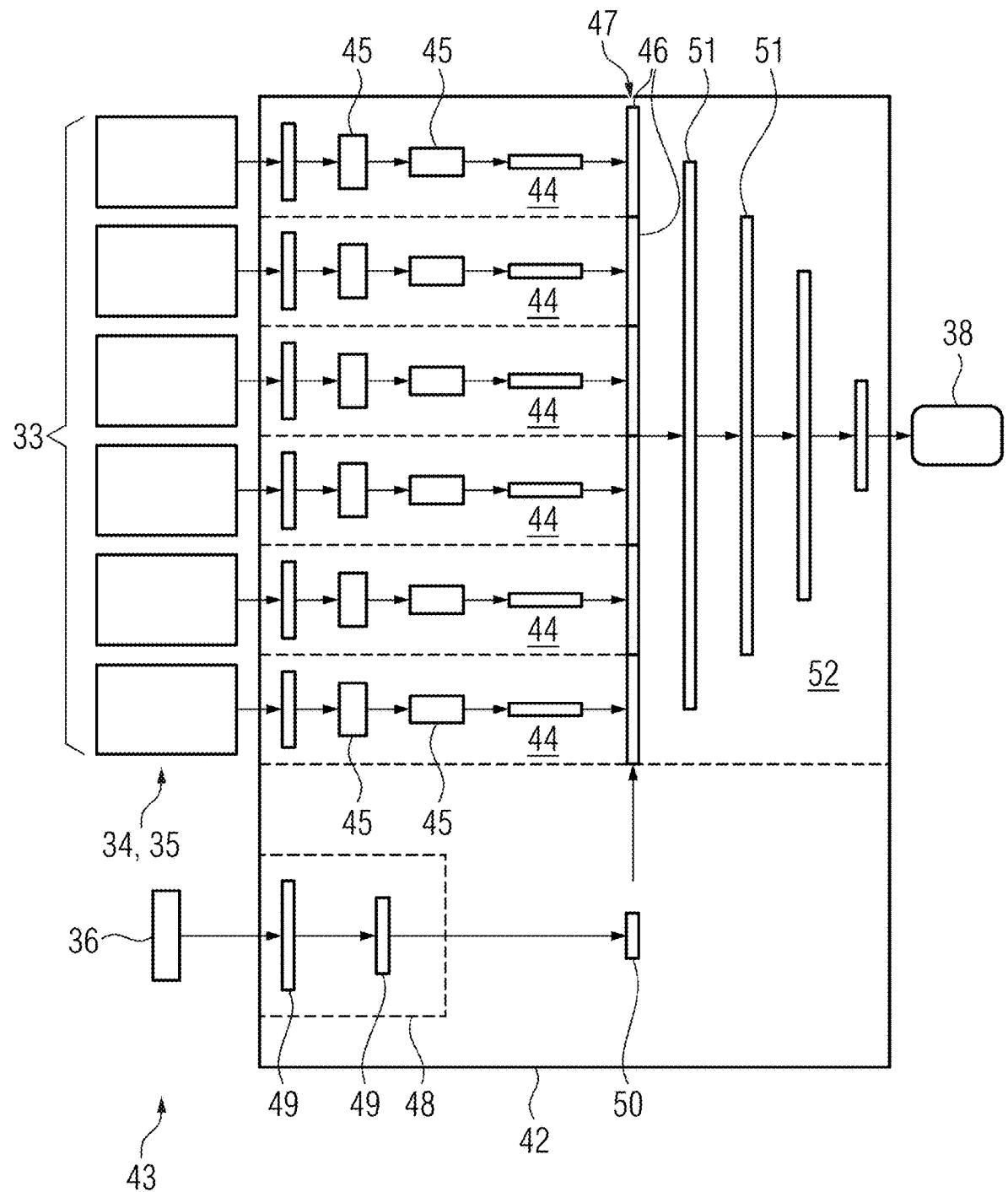
FIG. 4 illustrates an example structure of a neural network of a trained function, in accordance with one or more embodiments of the present disclosure.

FIG. 4 illustrates an example structure of a neural network 42 of a trained function, in accordance with one or more embodiments of the present disclosure. It is noted at this point that the topology shown is merely exemplary; a variety of other topologies may also be used.

To the left in FIG. 4, the input data 43 comprising the input data sets 33, e.g. the image data sets 34 and the parameter maps 35, and the additional information 36, are indicated. Each input data set 33 in this embodiment is input into a dedicated convolutional partial neural network 44, each comprising at least one convolutional layer 45. The convolutional partial neural networks 44 independently extract relevant features 46 from the respective input data sets 33. These features are concatenated, for example in a flattening layer, to a feature vector 47. The convolutional partial neural networks 44 may, of course, also comprise further layers, for example pooling layers.

As for the additional scalar and/or vector information 36, these are also analyzed to extract relevant features using a dense partial neural network 48 having at least one fully connected layer 49. The results are intermediate data 50, which are also added to the feature vector 47 by concatenation. It is noted that the dense partial neural network 48 is optional; it is also conceivable to add the additional information 36 directly to the feature vector 47.

The convolutional partial neural networks 44 and the dense partial neural network 48 can be understood as feature extractors.

The feature vector 47 is then fed through multiple fully connected layers 51 of a further dense partial neural network 52, which then gives the output data 38. It is noted that separate dense partial neural networks 52 may be provided for the at least one tissue score and the predictive outcome information, if this to be determined.

Figure 5:
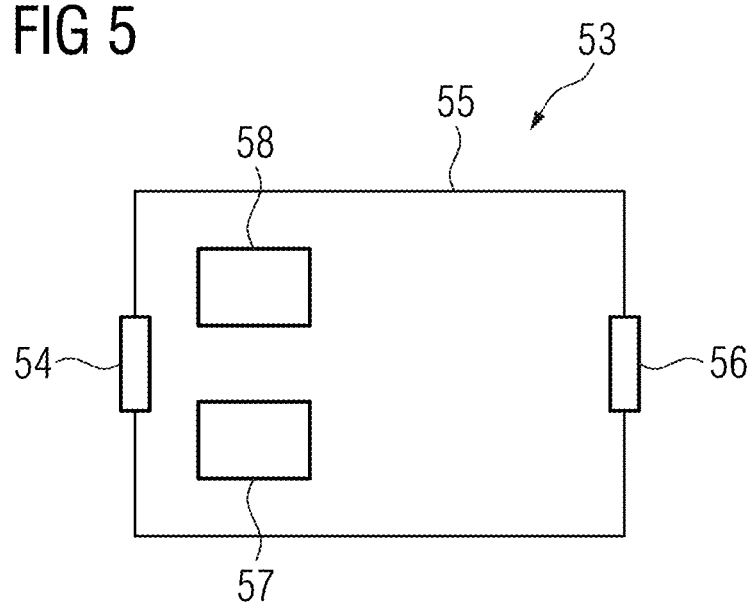
FIG. 5 illustrates an example characterization system, in accordance with one or more embodiments of the present disclosure.

FIG. 5 illustrates an example characterization system 53, in accordance with one or more embodiments of the present disclosure. The characterization system 53 is configured to perform the characterization method according to the embodiments of the disclosure and thus comprises a first interface 54 for receiving the input data 43, a computation unit 55 for analyzing the input data 43, and a second interface 56 for providing the output data 38. The computation unit 55, which may comprise at least one processor (e.g. processing circuitry, a CPU, one or more processors, etc.) and/or at least one storage means, comprises the trained function 57 as described above for performing step S2 and may additionally comprise a pre-processing sub-unit 58 to carry out step S1.

Figure 6:
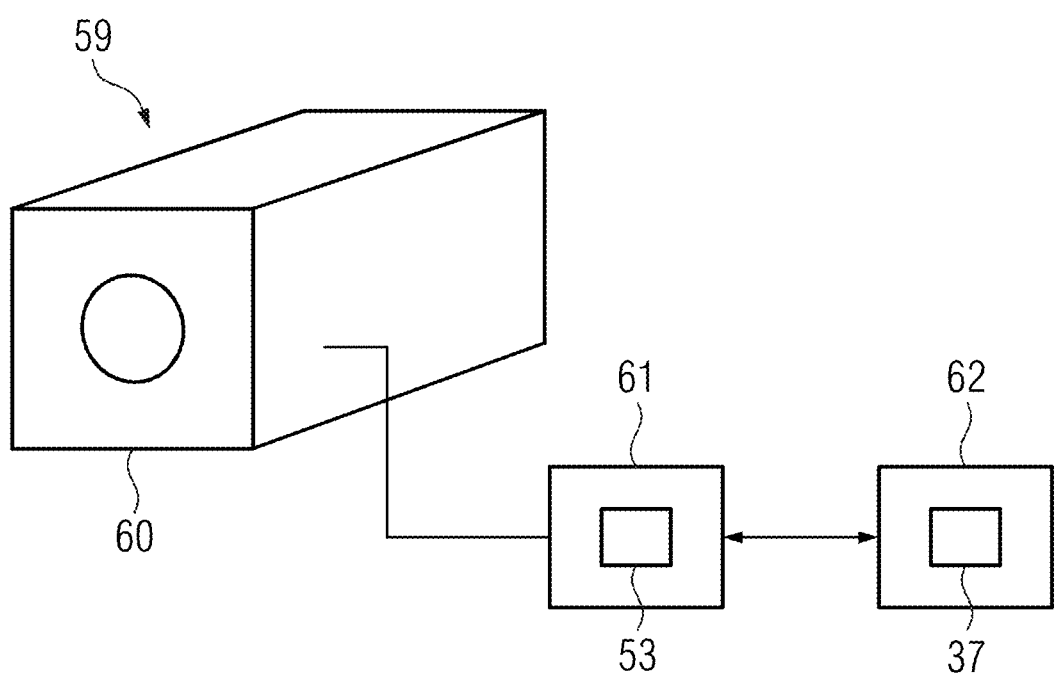
FIG. 6 illustrates an example magnetic resonance imaging device, in accordance with one or more embodiments of the present disclosure.

FIG. 6 illustrates an example magnetic resonance imaging device 59, in accordance with one or more embodiments of the present disclosure. The magnetic resonance imaging device 59 comprises, as known, a main magnet unit 60 housing the main field magnet and having a bore 60 into which a patient can be placed, for example using a patient table, for acquisition. The patient table as well as other typical components of a magnetic resonance imaging device 59, like gradient coils and high frequency coils, are not shown for purposes of brevity.

The magnetic resonance imaging device 59 is controlled using a control device 61, which may be implemented as one or more processors, processing circuitry, and alternatively be referred to as a controller or control computer. In this embodiment, a characterizing system 53 according to the disclosure is integrated into the control device 61, such that magnetic resonance input data sets 33 may be analyzed regarding the characterization of liver tissue on-site. To retrieve additional information 36 from electronic health records 37, the control device 61 may be connected to a database 62, for example via a local network or an internet connection or any suitable number and/or type of wired and/or wireless links.

Although the present disclosure has been described in detail with reference to the preferred embodiment, the present disclosure is not limited by the disclosed examples from which the skilled person is able to derive other variations without departing from the scope of the disclosure

What is claimed is:

1. A computer-implemented method for automatically characterizing liver tissue of a patient, comprising:
    receiving, via a first interface, a morphological magnetic resonance image data set and a magnetic resonance parameter map,
    wherein the morphological magnetic resonance image data set and the magnetic resonance parameter map are each acquired via a magnetic resonance imaging device;
    applying, via one or more processors, a trained function comprising a neural network to input data, the input data comprising the morphological magnetic resonance image data set and the magnetic resonance parameter map; and
    providing, via a second interface, generated output data comprising a tissue score describing the liver tissue,
    wherein the input data further comprises a magnetic resonance elastography data set of an imaging region comprising at least a portion of the liver tissue of the patient.

2. The method according to claim 1, wherein the tissue score comprises one or more of an nonalcoholic fatty liver disease (NAFLD) activity score, a steatosis score, a lobular inflammation score, a hepatocyte ballooning score, a fibrosis score, and/or a fibrosis stage.

3. The method according to claim 1, wherein the morphological magnetic resonance image data set comprises an image data set obtained via a fat-water separation technique.

4. The method according to claim 3, wherein the fat-water separation technique comprises a Dixon technique.

5. The method according to claim 1, wherein a parameter of the magnetic resonance parameter map includes one or more of relaxation times, a reciprocal of relaxation times, an extracellular fluid measure, and/or a fat fraction.

6. The method according to claim 5, wherein the reciprocal of relaxation times comprises R2*.

7. The method according to claim 1, wherein the input data further comprises a magnetic resonance diffusion.

8. The method according to claim 1, wherein the input data further comprises scalar and/or vector information related to the patient and/or related to the liver tissue of the patient.

9. The method according to claim 8, wherein the scalar and/or vector information includes one or more of demographic information, medical history information, and/or laboratory results.

10. The method according to claim 8, wherein the scalar and/or vector information is received from an electronic health record of the patient.

11. The method according to claim 1, wherein the neural network comprises:
    a convolutional layer in at least one convolutional partial neural network configured to extract features from the morphological magnetic resonance image data set and/or the magnetic resonance parameter map; and
    a fully connected layer in a dense partial neural network configured to derive the output data using the extracted features.

12. The method according to claim 11, wherein the one or more processors are further configured to, when the input data comprises scalar and/or vector information, add the scalar and/or vector information, or intermediate data derived therefrom, to a feature vector generated by the at least one convolutional partial neural network.

13. The method according to claim 12, wherein the intermediate data is generated by an additional dense partial neural network having at least one fully connected layer.

14. The method according to claim 1, wherein the output data further comprises predictive outcome information including risk scores for events related to liver tissue.

15. The method according to claim 1, wherein the trained function further comprises an uncertainty estimation subfunction that is configured to determine at least one uncertainty information regarding the output data, and
    wherein the second interface is further configured to provide the output data including the at least one uncertainty information.

16. The method according to claim 1, wherein the morphological magnetic resonance image data set and the magnetic resonance parameter map are from among a plurality of morphological magnetic resonance image data sets and a plurality of magnetic resonance parameter maps, respectively, and
    wherein the one or more processors are configured to perform a preprocessing step comprising:
        registering each one of the plurality of morphological magnetic resonance image data sets and each one of the plurality of magnetic resonance parameter maps to one other; and/or
        segmenting a region of interest to be analyzed by the trained function in each one of the plurality of morphological magnetic resonance image data sets and each one of the plurality of magnetic resonance parameter maps.

17. A characterization system for automatically characterizing liver tissue of a patient, comprising:
    a first interface configured to receive a morphological magnetic resonance image data set and a magnetic resonance parameter map,
    wherein the morphological magnetic resonance image data set and the magnetic resonance parameter map are each associated with an imaging region comprising at least a portion of the liver tissue of the patient and are acquired via a magnetic resonance imaging device;
    one or more processors configured to apply a trained function comprising a neural network to input data, the input data comprising the morphological magnetic resonance image data set and the magnetic resonance parameter map; and
    a second interface configured to provide generated output data comprising a tissue score describing the liver tissue,
    wherein the input data further comprises a magnetic resonance elastography data set of an imaging region comprising at least a portion of the liver tissue of the patient.

18. A non-transitory computer-readable medium comprising instructions which, when executed by one or more processors of a characterization system, cause the characterization system to:
- receive, via a first interface, a morphological magnetic resonance image data set and a magnetic resonance parameter map,
- wherein the morphological magnetic resonance image data set and the magnetic resonance parameter map are each associated with an imaging region comprising at least a portion of a liver tissue of a patient and are acquired via a magnetic resonance imaging device;
- apply a trained function comprising a neural network to input data, the input data comprising the morphological magnetic resonance image data set and the magnetic resonance parameter map; and
- provide, via a second interface, generated output data comprising a tissue score describing the liver tissue of the patient,
- wherein the input data further comprises a magnetic resonance elastography data set of an imaging region comprising at least a portion of the fiver tissue of the patient.

19. The method according to claim 1, wherein the magnetic resonance elastography data set provides information related to a stiffness of the liver tissue and is acquired using magnetic resonance elastography (MRE).

20. The method according to claim 7, wherein magnetic resonance diffusion-weighted data set comprises an apparent diffusion coefficient (ADC) map.

* * * * *